United States Patent [19]
Yagawara et al.

[11] Patent Number: 5,147,523
[45] Date of Patent: Sep. 15, 1992

[54] THIN FILM GAS SENSOR

[75] Inventors: Shinji Yagawara; Wasaburo Ohta, both of Yokohama, Japan

[73] Assignee: Ricoh Company, Ltd., Tokyo, Japan

[21] Appl. No.: 712,410

[22] Filed: Jun. 10, 1991

[30] Foreign Application Priority Data

Jun. 11, 1990 [JP] Japan .................. 2-152140
Aug. 30, 1990 [JP] Japan .................. 2-228851
Sep. 10, 1990 [JP] Japan .................. 2-239694
Jan. 30, 1991 [JP] Japan .................. 3-29578

[51] Int. Cl.⁵ .......................................... G01N 27/26
[52] U.S. Cl. ........................................... 204/424
[58] Field of Search .................. 204/424; 338/34; 73/31.06

[56] References Cited
U.S. PATENT DOCUMENTS 4,839,020 6/1989 Yamaguchi et al. ............ 204/424
5,003,812 2/1991 Yagawara ........................ 338/34

FOREIGN PATENT DOCUMENTS

59-89763 5/1984 Japan .
1167645 7/1989 Japan .

Primary Examiner—John Niebling
Assistant Examiner—Bruce Bell
Attorney, Agent, or Firm—Oblon, Spivak, McClelland, Maier & Neustadt

[57] ABSTRACT

A gas sensor senses gas using a metal oxide semiconductor whose resistance changes depending on gas adhesion on a surface of the metal oxide semiconductor. The gas sensor includes a base structure, and a gas sensitive layer formed on the base structure and made of a metal oxide semiconductor. The gas sensitive layer has a multi-layer structure which includes at least two layer portions having mutually different grain structures.

25 Claims, 9 Drawing Sheets

THIN FILM GAS SENSOR

BACKGROUND OF THE INVENTION

The present invention generally relates to gas sensors, and more particularly to a gas sensor for sensing gas existing within the atmosphere.

Gas sensors which use a metal oxide semiconductor as a gas sensitive material are known. In such gas sensors, a heater layer is provided on a back side of a metal oxide semiconductor layer via electrodes and an insulator layer or, an electrode and a heater coil which also functions as an electrode are provided within a metal oxide semiconductor. The gas sensor senses the gas using the fact that the resistance of the metal oxide semiconductor heated by the heater layer or the heater coil changes depending on the gas adhesion at the surface of the gas sensor.

Figure 1A:
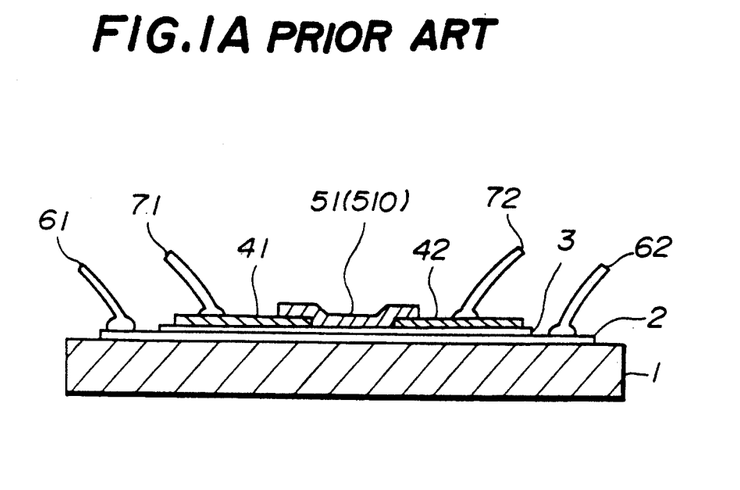
FIGS. 1A and 1B are a cross sectional view and a perspective view respectively showing an example of a conventional thin film gas sensor.
Figure 1B:
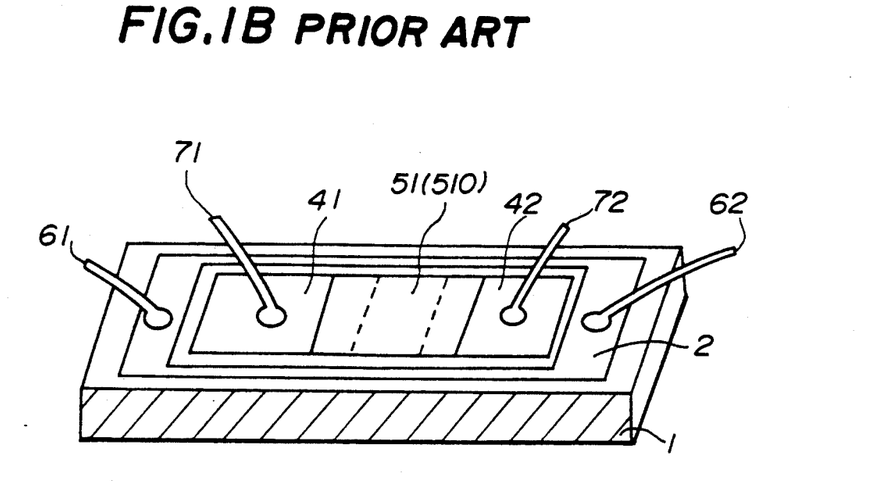

FIGS. 1A and 1B respectively show a cross section and a perspective view of an example of a thin film gas sensor. A heater layer 2 is formed on a heat resistant substrate 1, and an insulator layer 3 is formed on the heater layer 2. Electrodes 41 and 42 and a gas sensitive layer 51 are formed on the insulator layer 3. The gas sensitive layer 51 partially overlaps the electrodes 41 and 42. An insulator layer (not shown) is provided between the substrate 1 and the heater layer 2 if the substrate 1 is made of a conductive material. Power supply lines 61 and 62 for supplying power to the heater layer 2 connect to the heater layer 2. An output signal from the gas sensitive layer 51 is obtained via lead wires 71 and 72.

Figure 2:
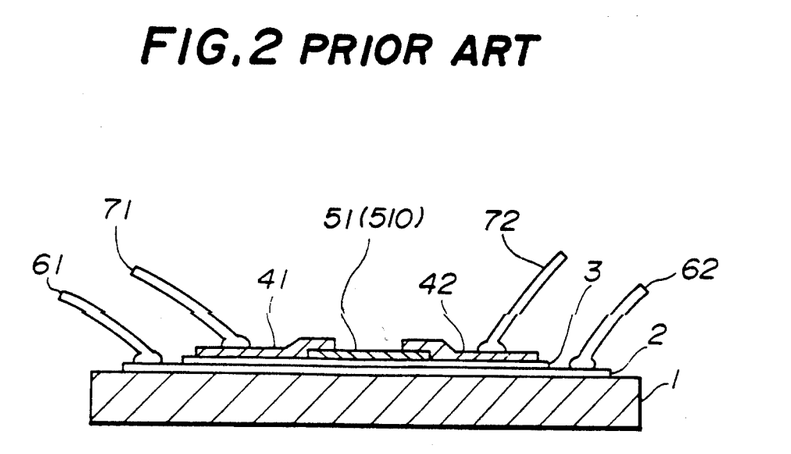
FIG. 2 is a cross sectional view showing another example of a conventional thin film gas sensor.

FIG. 2 shows a cross section of another example of a conventional thin film gas sensor. In FIG. 2, those parts which are the same as those corresponding parts in FIGS. 1A and 1B are designated by the same reference numerals, and a description thereof will be omitted. In FIG. 2, the electrodes 41 and 42 respectively overlap parts of the gas sensitive layer 51.

Figure 3:
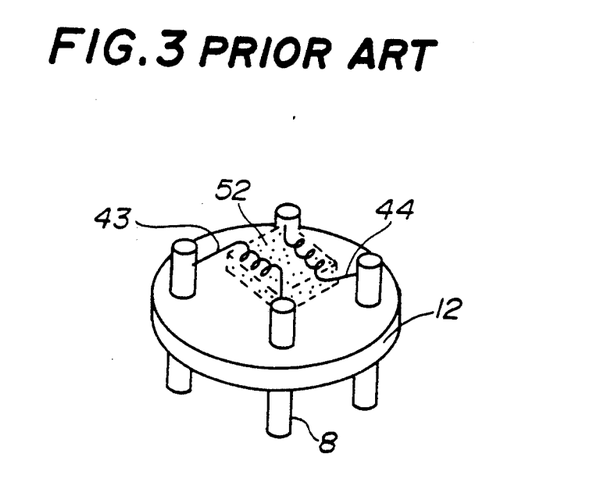
FIG. 3 is a perspective view showing still another example of a conventional gas sensor.

On the other hand, FIG. 3 shows a perspective view of still another example of a conventional gas sensor. Heater coils 43 and 44 also function as a pair of electrodes, and a sintered body (gas sensitive material) 52 made of a metal oxide semiconductor is supported between the heater coils 43 and 44. For example, the gas sensitive material 52 has a square shape in which each side is 2 to 3 mm long. Lead wires (not shown) can be connected to the heater coils (electrodes) 43 and 44 so as to obtain an output signal of the gas sensitive material 52. In addition, the heater coils 43 and 44 are embedded within the gas sensitive material 52. This gas sensor also includes a base 12 and electrode pins 8.

However, the gas sensor of the type shown in FIG. 3 has a large power consumption, and the response characteristic is poor because of the large thermal capacity. On the other hand, both the power consumption and response characteristic of the thin film gas sensors shown in FIGS. 1 and 2 are satisfactory, but the sensor characteristics greatly change with time. For this reason, the thin film gas sensors are not suited for practical use.

It may be regarded that the sensor characteristic of the thin film gas sensor deteriorates with time because the size of the crystal grains of the metal oxide semiconductor increases with time. Normally, the gas sensor is used at relatively high temperatures of 300° to 450° C. Hence, when the gas sensor is used under such a relatively high temperature for a long period of time, it may be regarded that the size of the crystal grains of the metal oxide semiconductor increases and the gas adhesion area decreases or the chemical activity decreases, thereby deteriorating the gas sensitivity.

SUMMARY OF THE INVENTION

Accordingly, it is a general object of the present invention to provide a novel and useful gas sensor in which the problems described above are eliminated.

Another and more specific object of the present invention is to provide a gas sensor which senses gas using a metal oxide semiconductor whose resistance changes depending on gas adhesion on a surface of the metal oxide semiconductor, comprising a base structure, and a gas sensitive layer formed on the base structure and made of a metal oxide semiconductor, where the gas sensitive layer has a multi-layer structure which includes at least two layer portions having mutually different grain structures. According to the gas sensor of the present invention, it is possible to ensure a stable sensor characteristic even after the gas sensor is used for a long period of time.

Still another object of the present invention is to provide a gas sensor of the type described above having the gas sensitive layer with the multi-layer structure, where the gas sensitive layer includes a lower layer portion which has a fine-grain structure and is formed on the base structure, and an upper layer portion which has a continuous layer structure and is formed on the lower layer portion.

A further object of the present invention is to provide a gas sensor of the type described above having the gas sensitive layer with the multi-layer structure, where the gas sensitive layer includes a lower layer portion which has a columnar grain structure and is formed on the base structure, an intermediate layer portion which has a fine-grain structure and is formed on the lower layer portion, and an upper layer portion which has a continuous layer structure and is formed on the intermediate layer portion, where the columnar grain structure includes grains which are arranged approximately perpendicularly to the base structure in the form of columns.

Another object of the present invention is to provide a gas sensor of the type described above having the gas sensitive layer with the multi-layer structure, where the gas sensitive layer includes a lower layer portion which has a columnar grain structure and is formed on the base structure, and an upper layer portion which has a fine-grain structure and is formed on the lower layer portion, where the columnar grain structure includes grains which are arranged approximately perpendicularly to the base structure in the form of columns.

Still another object of the present invention is to provide a gas sensor of the type described above having the gas sensitive layer with the multi-layer structure, where the gas sensitive layer includes a lower layer portion which has a columnar grain structure and is formed on the base structure, and an upper layer portion which has a continuous layer structure and is formed on the lower layer portion, where the columnar grain structure includes grains which are arranged approximately perpendicularly to the base structure in the form of columns.

Other objects and further features of the present invention will be apparent from the following detailed description when read in conjunction with the accompanying drawings.

DESCRIPTION OF THE PREFERRED EMBODIMENTS

The present inventors studied the sensor characteristic deterioration of the gas sensor with time, and found that the sensor characteristic deteriorates with time due to the increase of the crystal grain size of the metal oxide semiconductor which is used in the gas sensor. Normally, the gas sensor is used under a relatively high temperature of 300° to 450° C., and the crystallization of the metal oxide semiconductor progresses when the gas sensor is used under such a relatively high temperature for a long period of time. As a result, the crystal grain size of the metal oxide semiconductor increases and causes a decrease of the gas adhesion area or a decrease in the chemical activity, thereby deteriorating the gas sensitivity.

On the other hand, when the gas sensor is used under a condition such that the gas sensor is intermittently heated, the temperature cycle between room temperature and the relatively high temperature causes tension or compression stress in the gas sensor due to the differences of the coefficients of thermal expansion of the metal oxide semiconductor and the other layers including the substrate. The distortion caused by the tension or stress is relieved by the slip of the dislocation and the growth of hillock. When the distortion occurs, the gas sensitivity or the resistance of the metal oxide semiconductor.

In order to prevent the undesirable phenomenon described above, it is necessary to take the following measures. First, the gas sensor must have a structure which makes it difficult for the crystal grain size to increase or, the gas sensor must have a structure in which the metal oxide semiconductor thin film has a relatively large surface area so that a slight change in the surface area is negligible. Second, when the gas sensor is used in an environment which causes intermittent heating of the gas sensor, the gas sensor must have a structure which prevents a sudden temperature change of the metal oxide semiconductor thin film. Third, the gas sensor must have a structure such that accumulation of the distortion caused by the stress is prevented. The present inventors have studied the metal oxide semiconductor thin film from various aspects, and derived a metal oxide semiconductor thin film having a structure which satisfies the above conditions.

In other words, the present inventors have found the following from the studies on the metal oxide semiconductor thin film from the various aspects. It was found that the first condition described above can be satisfied by employing a metal oxide semiconductor thin film having a layer portion with a fine-grain structure. It was found that the second condition described above can be satisfied by covering the layer portion having the fine-grain structure by a continuous creasy layer portion so that a sudden temperature change is suppressed by an air layer existing between the two layer portions. In addition, it was found that the third condition described above can be satisfied by using a layer portion with a columnar grain structure which efficiently relieves the distortion between the metal oxide semiconductor thin film and the substrate caused by the temperature cycle. Hence, the above findings are effectively combined in the present invention.

In the present invention, it is desirable that the metal oxide semiconductor thin film has the layer portion with the fine-grain structure in which the average grain diameter is 0.005 to 5 μm, and preferably 0.03 to 0.1 μm. In addition, it is desirable that the layer portion with the columnar grain structure have the grains arranged approximately perpendicularly to the substrate in the form of columns, where the average grain diameter is 0.005 to 5 μm. Furthermore, it is desirable that the layer portion having the fine-grain structure or the columnar grain structure forms at least 1/10 of the entire metal oxide semiconductor thin film.

The present inventors produced four kinds of metal oxide semiconductor thin films and subjected the metal oxide semiconductor thin films to a heat cycle which changes between room temperature and 450° C. As a result, it was confirmed that the gas sensitivity does not deteriorate even after 200,000 heat cycles.

Next, a description will be given of a method of forming the metal oxide semiconductor thin film having the above described structure. The material used for the metal oxide semiconductor thin film is not limited to a particular material. However, preferable examples of the metal oxide semiconductor are oxides of tin, titanium, indium, nickel, tungsten, cadmium, iron and zinc. The total thickness of the metal oxide semiconductor thin film is 1000 to 20000 Å, and preferably 3000 to 8000 Å. The thickness of an upper layer portion of the metal oxide semiconductor thin film is 200 to 5000 Å, and preferably 1000 to 2000 Å. The thickness of an intermediate layer portion of the metal oxide semiconductor thin film is 500 to 10000 Å, and preferably 1000 to 3000 Å. The thickness of a lower layer portion of the metal oxide semiconductor thin film is 300 to 5000 Å, and preferably 1000 to 3000 Å.

The metal oxide semiconductor thin film may be formed by methods such as vapor deposition and sputtering. Preferably, the metal oxide semiconductor thin film is formed by evaporation employed in a thin film evaporation apparatus proposed in a Japanese Laid-Open Patent Application No. 59-89763. In the embodiments described in the following, it is assumed for the sake of convenience that the thin film evaporation apparatus used is the apparatus proposed in the Japanese Laid-Open Patent Application No. 59-89763.

In addition, the present invention may be applied to various gas sensors other than the gas sensors shown in FIGS. 1 and 2. For example, the present invention may be applied to a gas sensor which has a micro-heater structure and proposed in a U.S. Pat. No. 4,967,589 (or Japanese Laid-Open Patent Application No. 1-167645), as will be described later.

Next, a description will be given of a first embodiment of the gas sensor according to the present invention. Tin is used as the evaporating metal, and the pressure within an evaporation chamber of an evaporation apparatus is preset to $1/10^4$ Pa before introducing oxygen gas within the substantially vacuum evaporation chamber. Then, the pressure within the evaporation chamber is set to 1 Pa and a current on the order of 70 A is applied to a filament to generate thermoelectrons. In addition, a voltage on the order of 100 V is applied to grids to generate oxygen plasma. Tin is evaporated in this state to form a tin oxide thin film 510 on a substrate structure 600 at a growth rate of 20 Å/sec. Thereafter, an annealing is carried out for approximately 3 hours in the oxygen atmosphere at approximately 700° C. For example, the substrate structure 600 includes the substrate 1, the heater layer 2 and the insulator layer 3 which are stacked as shown in FIGS. 1 and 2, and of course, another insulator layer may be interposed between the substrate 1 and the heater layer 2 if the substrate 1 is conductive.

Figure 4A:
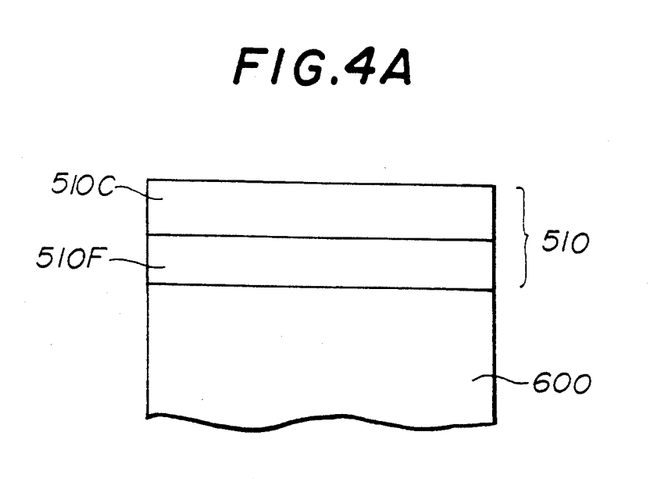
FIG. 4A is a cross sectional view showing an essential part of a first embodiment of a gas sensor according to the present invention.
Figure 4B:
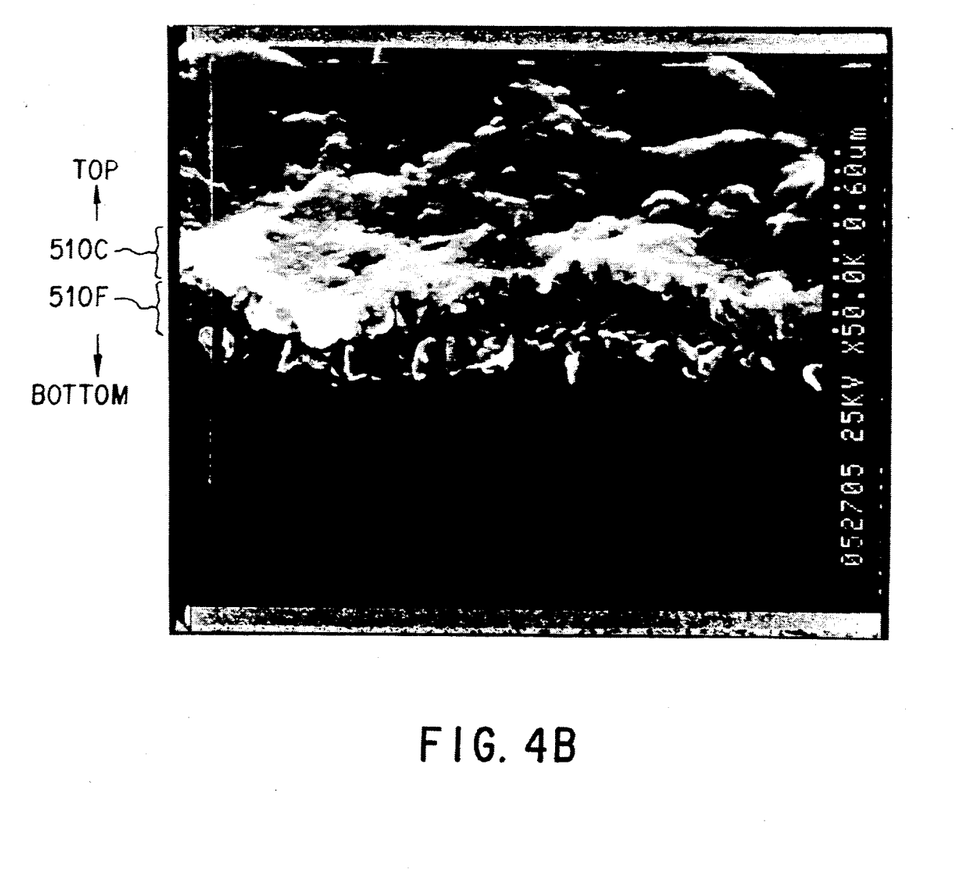
FIG. 4B is a SEM photograph showing a cross section of an essential part of the first embodiment.

FIG. 4A shows a cross section of the first embodiment, and FIG. 4B shows a scanning electron microscope (SEM) photograph of a cross section of the tin oxide thin film portion of the first embodiment. The SEM photograph shows the cross section with a magnification of 50,000 times. The tin oxide thin film 510 as a whole has a thickness of approximately 0.3 μm. An upper layer portion 510C of the tin oxide thin film 510 has a continuous layer structure with a thickness of approximately 0.1 μm. A lower layer portion 510F of the tin oxide thin film 510 has a fine-grain structure with a grain diameter of approximately 0.03 to 0.1 μm. In addition, the thickness of the lower layer portion 510F must be greater than or equal to 1/10 the total thickness of the tin oxide thin film 510 in order to suppress the distortion between the substrate structure 600 and the tin oxide thin film 510. The first embodiment of the gas sensor was tested and the superb sensor characteristic was confirmed.

Next, a description will be given of a second embodiment of the gas sensor according to the present invention. Tin is used as the evaporating metal, and the pressure within an evaporation chamber of an evaporation apparatus is preset to $1/10^4$ Pa before introducing oxygen gas within the substantially vacuum evaporation chamber. Then, the pressure within the evaporation chamber is set to 0.2 Pa and a current on the order of 70 A is applied to a filament to generate thermoelectrons. In addition, a voltage on the order of 100 V is applied to grids to generate oxygen plasma. Tin is evaporated in this state to form a tin oxide thin film 510 on a substrate structure 600 at a growth rate of 22 Å/sec. Thereafter, an annealing is carried out for approximately 3 hours in the oxygen atmosphere at approximately 700° C.

Figure 5A:
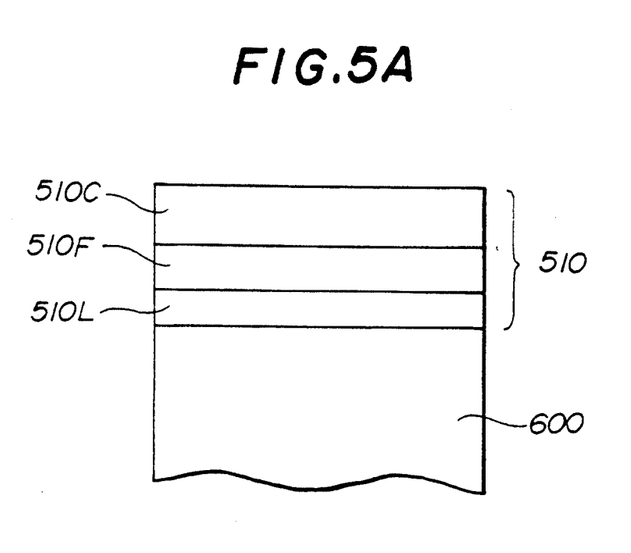
FIG. 5A is a cross sectional view showing an essential part of a second embodiment of the gas sensor according to the present invention.
Figure 5B:
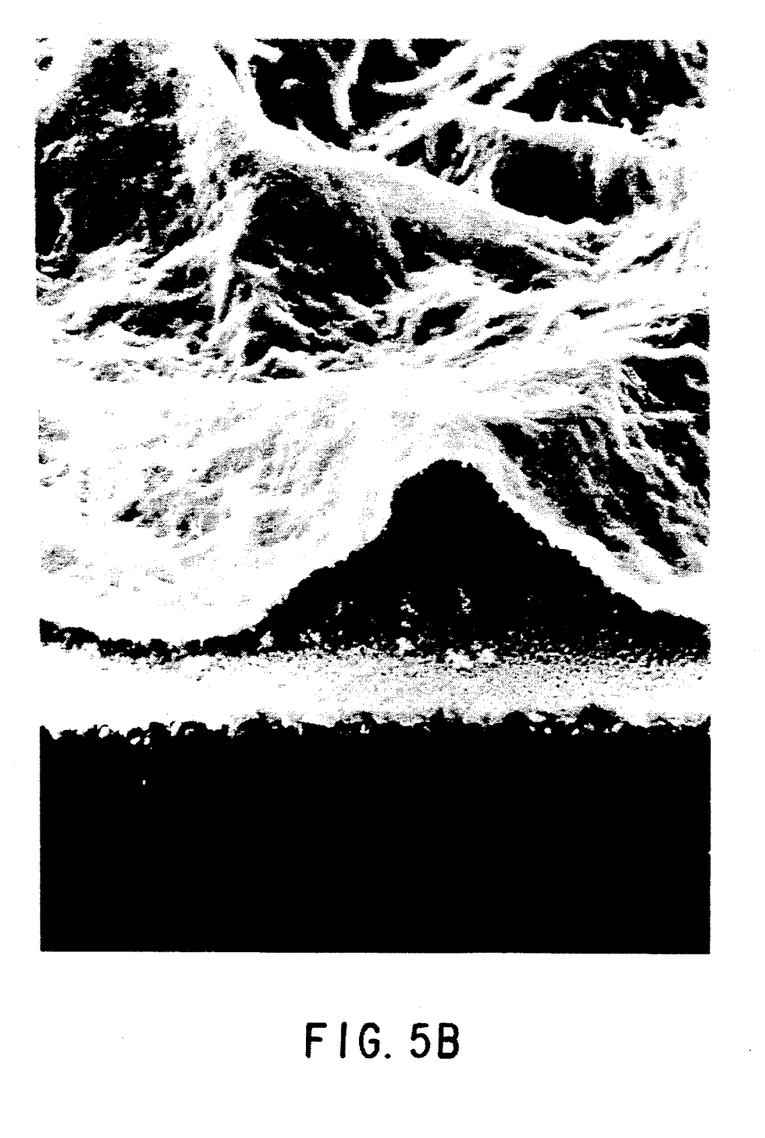
FIG. 5B is a SEM photograph showing a cross section of an essential part of the second embodiment.

FIG. 5A shows a cross section of the second embodiment, and FIG. 5B shows a SEM photograph of a cross section of the tin oxide thin film portion of the second embodiment. The SEM photograph shows the cross section with a magnification of 10,000 times. The tin oxide thin film 510 as a whole has a thickness of approximately 0.5 μm, and the tin oxide thin film 510 is made up of a creasy upper layer portion 510C having a continuous layer structure, a fine-grain intermediate layer portion 510F and a lower layer portion 510L having a columnar grain structure.

Figure 6:
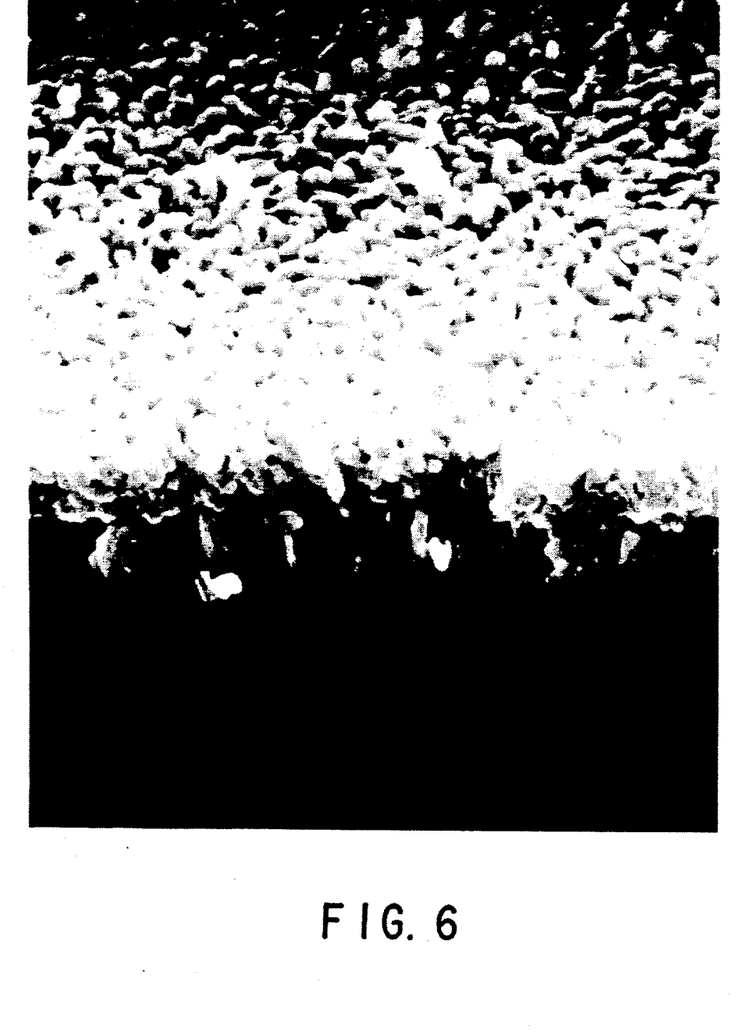
FIG. 6 is a SEM photograph showing a cross section of an essential part of the second embodiment on an enlarged scale.

FIG. 6 shows the intermediate and lower layer portions 510F and 510L of the second embodiment on an enlarged scale. This SEM photograph shows the cross section with a magnification of 50,000 times. In FIG. 6, the grains of the intermediate layer portion 510F have a grain diameter of approximately 200 to 1000 Å. The columnar grains of the lower layer portion 510L have a grain diameter of approximately 200 to 1000 Å. The grain diameters of the grains of the intermediate layer portion 510F and the columnar grains of the lower layer portion 510L are dependent on the thickness of the metal oxide used, but are preferably on the order of 100 to 2000 Å. In addition, the thickness of the lower layer portion 510L needs to be greater than or equal to 1/10 the total thickness of the tin oxide thin film 510 in order to suppress the distortion between the substrate structure 600 and the tin oxide thin film 510. The second embodiment of the gas sensor was tested and the superb sensor characteristic was confirmed.

Figure 7:
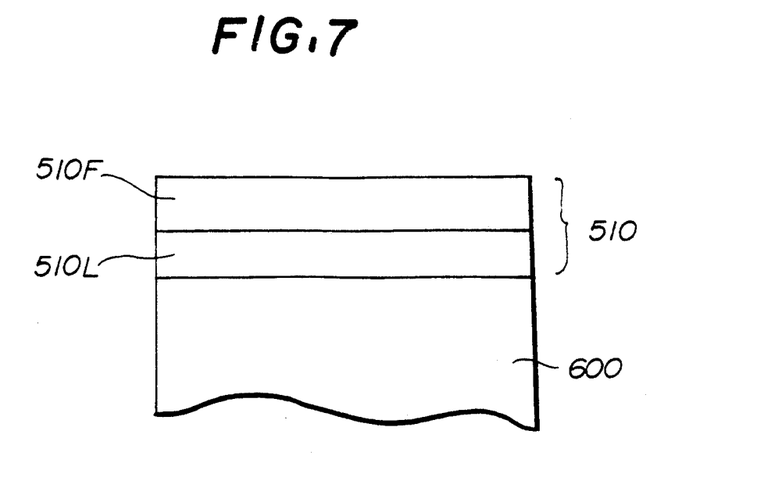
FIG. 7 is a cross sectional view showing an essential part of a third embodiment of the gas sensor according to the present invention.

Next, a description will be given of a third embodiment of the gas sensor according to the present invention. This embodiment is produced by removing only the upper layer portion 510C of the tin oxide thin film 510 of the second embodiment. The upper layer portion 510C may be removed by mechanical means, etching or the like. Hence, in this embodiment, the tin oxide thin film 510 of the gas sensor is made up of an upper layer portion 510F which has the fine-grain structure and a lower layer portion 510L which has the columnar grain structure as shown in FIG. 7. The third embodiment of the gas sensor was tested and the superb sensor characteristic was confirmed.

Figure 8:
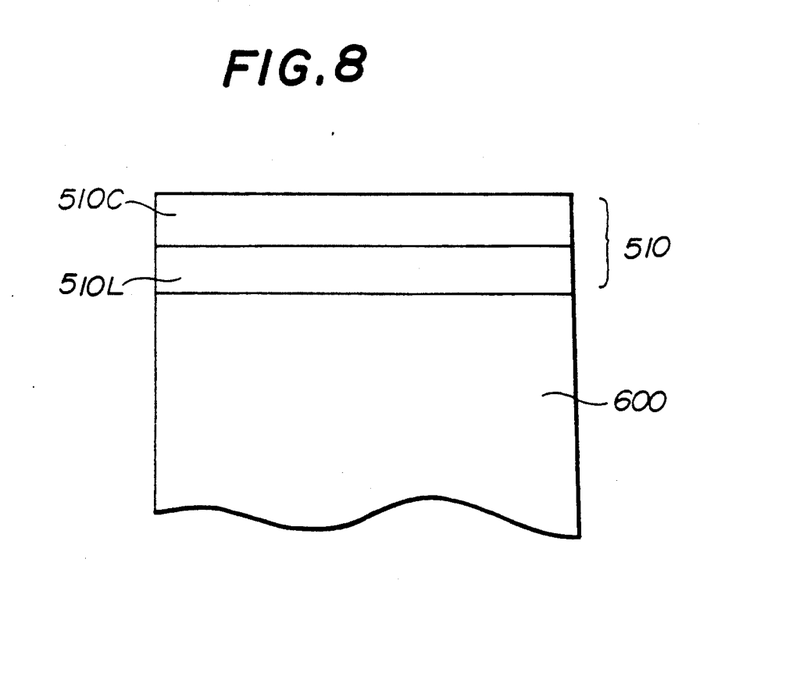
FIG. 8 is a cross sectional view showing an essential part of a fourth embodiment of the gas sensor according to the present invention.

FIG. 8 shows a fourth embodiment of the gas sensor according to the present invention. In this embodiment, the tin oxide thin film 510 is made up of an upper layer portion 510C having the continuous layer structure and a lower layer portion 510L having the columnar grain structure. The lower layer portion 510L has a thickness which is at least 1/10 the total thickness of the tin oxide thin film 510. The fourth embodiment of the gas sensor was tested and the superb sensor characteristic was confirmed.

The tin oxide thin film 510 of the embodiments described above may be used in place of the gas sensitive layer 51 shown in FIGS. 1 and 2. Furthermore, the tin oxide thin film 510 may be used in place of a gas sensitive layer of any type of thin film gas sensor. For example, the tin oxide thin film 510 may be applied to the gas sensors disclosed in the U.S. Pat. No. 4,967,589 having the micro-heater structure.

Figure 9:
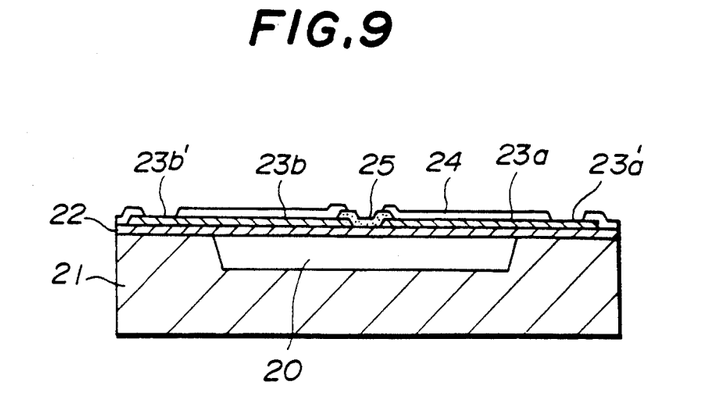
FIG. 9 is a cross sectional view showing an essential part of a gas sensor modified in accordance with the present invention.

FIG. 9 shows a cross section of one of the gas sensors proposed in the U.S. Pat. No. 4,967,589. The gas sensor shown in FIG. 9 includes a silicon substrate 21 which has a cavity 20, an insulator layer 22, a pair of detection leads 23a and 23b, bonding pads 23a' and 23b', an insulation coating layer 24 and a gas sensitive layer 25 which are arranged as shown. The tin oxide thin film 510 may be used in place of the gas sensitive layer 25. The gas sensors having the micro-heater structure are further disclosed in the U.S. Pat. No. 4,967,589, the disclosure of which is hereby incorporated by reference.

Figure 10:
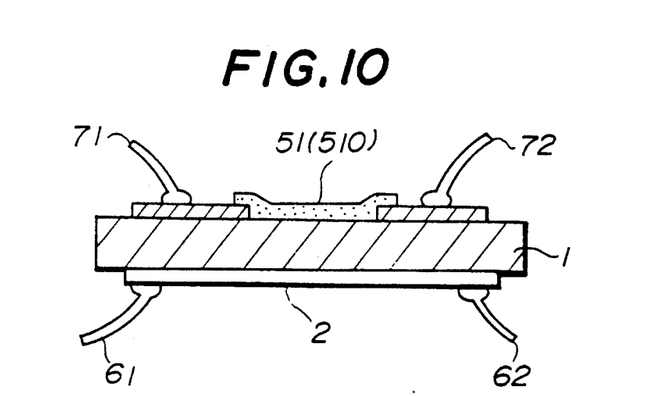
FIG. 10 is a cross sectional view showing still another gas sensor to which the present invention may be applied.

FIG. 10 shows a cross section of still another gas sensor to which the present invention may be applied. In FIG. 10, those parts which are the same as those corresponding parts in FIGS. 1 and 2 are designated by the same reference numerals, and a description thereof will be omitted. In FIG. 10, the gas sensitive layer 51 is formed on the substrate 1, and the substrate 1 is formed on the heater layer 2. The tin oxide thin film 510 of the embodiments described above may be used in place of the gas sensitive layer 51.

Of course, the metal oxide semiconductor used for the gas sensitive layer is not limited to the tin oxide used in the described embodiments. As described above, preferable examples of the metal oxide semiconductor are oxides of tin, titanium, indium, nickel, tungsten, cadmium, iron and zinc.

Further, the present invention is not limited to these embodiments, but various variations and modifications may be made without departing from the scope of the present invention.

What is claimed is:

1. A gas sensor which senses gas using a metal oxide semiconductor whose resistance changes depending on gas adhesion on a surface of the metal oxide semiconductor, said gas sensor comprising:
a base structure; and
a gas sensitive layer formed on said base structure and made of a metal oxide semiconductor,
said gas sensitive layer having a multi-layer structure which includes at least two layer portions having mutually different grain structures.

2. The gas sensor as claimed in claim 1, wherein said gas sensitive layer includes a lower layer portion which has a fine-grain structure and is formed on said base structure, and an upper layer portion which has a continuous layer structure and is formed on the lower layer portion.

3. The gas sensor as claimed in claim 2, wherein said lower layer portion is made up of grains having an average diameter of 0.005 to 5 μm.

4. The gas sensor as claimed in claim 2, wherein said lower layer portion has a thickness which is at least 1/10 of a total thickness of said gas sensitive layer.

5. The gas sensor as claimed in claim 2, wherein said gas sensitive layer is made of a metal oxide material selected from a group consisting of oxides of tin, titanium, indium, nickel, tungsten, cadmium, iron and zinc.

6. The gas sensor as claimed in claim 2, wherein said base structure includes a heater layer and an insulator layer which is formed on the heater layer, said gas sensitive layer being formed on the insulator layer.

7. The gas sensor as claimed in claim 2, wherein said base structure includes a substrate having first and second surfaces and a heater layer formed on the first surface of the substrate, said gas sensitive layer being formed on the second surface of the substrate.

8. The gas sensor as claimed in claim 1, wherein said gas sensitive layer includes a lower layer portion which has a columnar grain structure and is formed on said base structure, an intermediate layer portion which has a fine-grain structure and is formed on the lower layer portion, and an upper layer portion which has a continuous layer structure and is formed on the intermediate layer portion, said columnar grain structure including grains which are arranged approximately perpendicularly to said base structure in the form of columns.

9. The gas sensor as claimed in claim 8, wherein said lower and intermediate layer portions are respectively made up of grains having an average diameter of 0.005 to 5 μm.

10. The gas sensor as claimed in claim 8, wherein said lower layer portion has a thickness which is at least 1/10 of a total thickness of said gas sensitive layer.

11. The gas sensor as claimed in claim 8, wherein said gas sensitive layer is made of a metal oxide material selected from a group consisting of oxides of tin, titanium, indium, nickel, tungsten, cadmium, iron and zinc.

12. The gas sensor as claimed in claim 8, wherein said base structure includes a heater layer and an insulator layer which is formed on the heater layer, said gas sensitive layer being formed on the insulator layer.

13. The gas sensor as claimed in claim 8, wherein said base structure includes a substrate having first and second surfaces and a heater layer formed on the first surface of the substrate, said gas sensitive layer being formed on the second surface of the substrate.

14. The gas sensor as claimed in claim 1, wherein said gas sensitive layer includes a lower layer portion which has a columnar grain structure and is formed on said base structure, and an upper layer portion which has a fine-grain structure and is formed on the lower layer portion, said columnar grain structure including grains which are arranged approximately perpendicularly to said base structure in the form of columns.

15. The gas sensor as claimed in claim 14, wherein said lower and upper layer portions are respectively made up of grains having an average diameter of 0.005 to 5 μm.

16. The gas sensor as claimed in claim 14, wherein said lower layer portion has a thickness which is at least 1/10 of a total thickness of said gas sensitive layer.

17. The gas sensor as claimed in claim 14, wherein said gas sensitive layer is made of a metal oxide material selected from a group consisting of oxides of tin, titanium, indium, nickel, tungsten, cadmium, iron and zinc.

18. The gas sensor as claimed in claim 14, wherein said base structure includes a heater layer and an insulator layer which is formed on the heater layer, said gas sensitive layer being formed on the insulator layer.

19. The gas sensor as claimed in claim 14, wherein said base structure includes a substrate having first and second surfaces and a heater layer formed on the first surface of the substrate, said gas sensitive layer being formed on the second surface of the substrate.

20. The gas sensor as claimed in claim 1, wherein said gas sensitive layer includes a lower layer portion which has a columnar grain structure and is formed on said base structure, and an upper layer portion which has a continuous layer structure and is formed on the lower layer portion, said columnar grain structure including grains which are arranged approximately perpendicularly to said base structure in the form of columns.

21. The gas sensor as claimed in claim 20, wherein said lower layer portion is made up of grains having an average diameter of 0.005 to 5 μm.

22. The gas sensor as claimed in claim 20, wherein said lower layer portion has a thickness which is at least 1/10 of a total thickness of said gas sensitive layer.

23. The gas sensor as claimed in claim 20, wherein said gas sensitive layer is made of a metal oxide material selected from a group consisting of oxides of tin, titanium, indium, nickel, tungsten, cadmium, iron and zinc.

24. The gas sensor as claimed in claim 20, wherein said base structure includes a heater layer and an insulator layer which is formed on the heater layer, said gas sensitive layer being formed on the insulator layer.

25. The gas sensor as claimed in claim 20, wherein said base structure includes a substrate having first and second surfaces and a heater layer formed on the first surface of the substrate, said gas sensitive layer being formed on the second surface of the substrate.

* * * * *